United States Patent
Lyu et al.

(10) Patent No.: US 12,069,792 B2
(45) Date of Patent: Aug. 20, 2024

(54) PLASMA AEROSOL DEVICE

(71) Applicant: Feng Chia University, Taichung (TW)

(72) Inventors: Guan-Heng Lyu, Luye Township, Taitung County (TW); Ying-Hung Chen, Taichung (TW); Ping-Yen Hsieh, Tainan (TW); Tsung-Han Chen, Taichung (TW); Chu-Liang Ho, Taichung (TW)

(73) Assignee: FENG CHIA UNIVERSITY, Taichung (TW)

( * ) Notice: Subject to any disclaimer, the term of this patent is extended or adjusted under 35 U.S.C. 154(b) by 909 days.

(21) Appl. No.: 17/123,084

(22) Filed: Dec. 15, 2020

(65) Prior Publication Data
US 2022/0095444 A1    Mar. 24, 2022

(30) Foreign Application Priority Data

Sep. 23, 2020   (TW) .................................. 109132994

(51) Int. Cl.
*H05H 1/24*   (2006.01)
*A61L 2/14*   (2006.01)

(52) U.S. Cl.
CPC ............ *H05H 1/2406* (2013.01); *A61L 2/14* (2013.01); *H05H 1/2431* (2021.05)

(58) Field of Classification Search
CPC ....... A61L 2/14; H05H 1/2406; H05H 1/2431
See application file for complete search history.

(56) References Cited

U.S. PATENT DOCUMENTS

| | | | |
|---|---|---|---|
| 2003/0180421 A1 | 9/2003 | Ruan et al. | |
| 2007/0020159 A1* | 1/2007 | Tsui | F24F 8/192 422/186.04 |
| 2012/0089084 A1* | 4/2012 | O'Keeffe | A61L 26/0066 523/105 |
| 2016/0220714 A1* | 8/2016 | Weltmann | A61L 2/14 |
| 2017/0142962 A1* | 5/2017 | Tsai | C02F 1/4608 |
| 2018/0242577 A1 | 8/2018 | Tsai et al. | |
| 2023/0201392 A1* | 6/2023 | Canady | A61L 9/20 250/435 |

FOREIGN PATENT DOCUMENTS

| | | |
|---|---|---|
| CN | 104583131 A | 4/2015 |
| CN | 106414932 A | 2/2017 |
| CN | 109545648 A | 3/2019 |
| EP | 0789505 A1 | 8/1997 |
| GB | 2594500 A | 11/2021 |
| IT | 102017000064091 A1 | 12/2018 |
| WO | WO 2014104350 A1 * | 7/2014 |
| WO | 2019/175063 A1 | 9/2019 |
| WO | 2020/154655 A1 | 7/2020 |

OTHER PUBLICATIONS

Partial English Translation of WO 2014104350 A! (Year: 2014).*

* cited by examiner

*Primary Examiner* — Charles S Bushey
(74) *Attorney, Agent, or Firm* — Cheng-Ju Chiang

(57) ABSTRACT

The present invention discloses that a plasma aerosol device includes a gas tunnel, a dielectric barrier discharge module, and a liquid tunnel. The invention uses a mechanism similar to a dielectric barrier discharge (DBD) electrode system, thus to enable generating a plasma active water mist which riches in free radicals such as reactive nitrogen species (RNS) and reactive oxygen species (ROS). Therefore, this invention is able to be used in medical, sterilization, agriculture and preservation industries.

9 Claims, 2 Drawing Sheets

PLASMA AEROSOL DEVICE

TECHNICAL FIELD

The present invention relates to a plasma aerosol device. In particular, this invention refers to a principle similar to a dielectric barrier discharge (DBD) electrode system that enables the present invention to generate plasma active water mist, which riches in free radicals, and is able to be used in medical, sterilization, agriculture, and preservation industries.

BACKGROUND OF RELATED ARTS

The focus of food issues is the advancement of agricultural technology. In recent years, in order to reduce or even avoid the interference of plant diseases and insect pests, pesticides are generally applied during the planting process.

Pesticides are generally classified into chemical pesticides, biological pesticides or biochemical pesticides. However, no matter what kind of pesticide that may be harmful for the environment and people. Basically, in order to increase the yield of crops, the most commonly used method today is to spray a large amount of mature and relatively inexpensive chemical fertilizers. High-efficiency chemical fertilizers can greatly increase the rate of plant absorption, but the application and residues of chemical fertilizers still harm the environment and people.

Even if the planting process is well done and the crop is harvested, the huge economic losses and food safety issues are still caused by corruption during the transportation. The preservation process must be further considered. The reason is that the preservation and transportation of crops requires a clean environment. Once the crops suffered from microbial contamination in any process, the abovementioned situation may occur.

Therefore, transportation, related storage and dealing methods still cost a lot. Although in modern society, the preservation techniques of controlling the growth of microorganisms while supplying good nutrients to the crops or clean techniques of medical uses are still hard and insufficient.

SUMMARY

To resolve the drawbacks of the prior arts, the present invention discloses plasma aerosol device, comprising an air channel, a dielectric barrier discharge module, and a liquid channel.

The air channel includes an input and an output. The dielectric barrier discharge module is configured between the input and the output, and the dielectric barrier discharge module is mainly composed of at least two insulators, a first electrode, a power source, a dielectric material layer, and a second electrode.

The at least two insulators are configured in the air channel, and the first electrode is arranged and embedded in the at least two insulators. Furthermore, the power source is connected to the first electrode, and the second electrode is grounded and wrapped outside the dielectric material layer. The dielectric material layer is wrapped in the air channel where the first electrode is embedded. Finally, the liquid channel has a fogger, and the liquid channel is connected to the output.

The present invention is able to immediately improve the existing technology efficiencies and reduce related costs of the existing agricultural technology such as supply, transportation and preservation of crop nutrients or medical microbial control via high voltage, frequency and low energy consumption power.

The abovementioned summary of the present disclosure relates to provide a basic description of the various aspects and features of the invention. The invention is not to be construed as being limited to the details of the present disclosure.

DETAILED DESCRIPTION OF THE INVENTION

To clarify the purpose, technical solutions, and the advantages of the disclosure, embodiments of the present disclosure will now be described more fully hereinafter with reference to the accompanying drawings.

Figure 1:
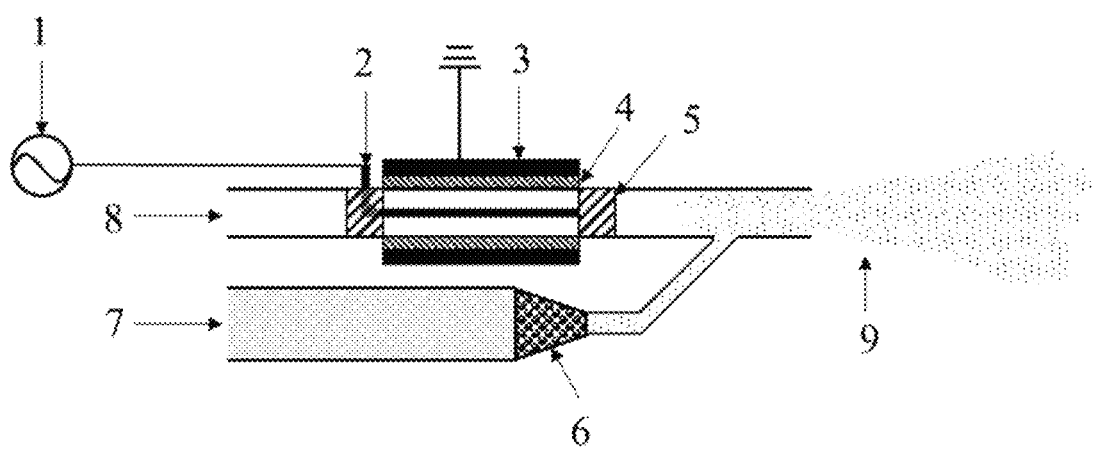
FIG. 1 is a schematic diagram of the structure of an embodiment of the present invention.

Please see FIG. 1, FIG. 1 is a schematic diagram of the structure of an embodiment of the present invention. As shown in FIG. 1, the present embodiment of the present invention provides a plasma aerosol device comprises an air channel 8, a dielectric barrier discharge module (including two insulators 5, a first electrode 2, a power source 1, a dielectric material layer 4, and a second electrode 3 in FIG. 1) and a liquid channel 7.

The air channel 8 of current embodiment comprises an input and an output. Referring to the embodiment of FIG. 1, for example, the left side of air channel 8 is the aforesaid input, and the right side is the aforesaid output. The abovementioned dielectric barrier discharge module of this embodiment is set between the input and the output, and the dielectric barrier discharge module is composed of two insulators 5, a first electrode 2, a power source 1, a dielectric material layer 4, and a second electrode 3.

In present embodiment, two insulators 5 are set in the air channel 8. Particularly, the insulator 5 is made of insulating materials such as high temperature resistant rubber, plastic, or their combination thereof. The insulator 5 of this embodiment also allowed to be designed into any shape that avoids disturbing the flow of gas in the air channel 8. Specifically, the capable shape of insulator 5 is able to be designed as a tube shape or a honeycomb shape, which is not limited thereto. The insulator 5 of this embodiment is designed to be integrated with (otherwise, inserted in) the air channel 8 by fitting, engaging or installing.

On the other hand, the possible purpose of the insulator 5 of this embodiment is available for the first electrode 2 passing through the insulator 5 per se. Therefore, this embodiment allows the first electrode 2 to be further exposed to the gas in the air channel 8. Furthermore, the first electrode 2 of this embodiment is connected to the power source 1. The power source 1 used in this embodiment may be a 110 V mains power source (mains electricity) which is an AC current converted into a high-frequency, high-voltage and low-energy consumption power source.

Specifically, the output frequency of the power carried by the power source 1 of this embodiment is not particularly limited, but must be higher than tens of kHz. Precisely, the power source 1 of this embodiment is between 10-100 kHz. The operating voltage of the power source 1 is also not particularly limited, but it must be higher than several kV, in fact, the power source 1 of the present embodiment is able to be set between 5-15 kV. Finally, the operating current of the power source 1 is not particularly limited, too. In this embodiment, in order to the requirement of low energy consumption, the available current of the power source 1 is suggested to be set less than 0.1 A. The suggested range of current is between 0.001-0.1 A.

The dielectric material layer 4 is wrapped in the air channel 8 and located in the place where the first electrode 2 is embedded. The second electrode 3 is configured in the form of grounding, and the second electrode 3 is wrapped outside the dielectric material layer 4. In this embodiment, the first electrode 2, the air channel 8 and the gas in the air channel 8, the dielectric material layer 4 and the second electrode 3 are co-constructed into a tubular-concentric-circles shape structure. Therefore, the present embodiment is able to be regarded as a structure of a tubular dielectric barrier discharge (DBD) electrode system.

The liquid channel 7 of this embodiment has a fogger 6, and the liquid channel 7 is connected to the output of the air channel 8 (Please refer to the right side of FIG. 1). In this embodiment, the liquid channel 7 is able to be regarded as any liquid storage container/pipeline with a pump or the device having similar functions. The present invention is not limited thereto. The fogger 6 of this embodiment can use a sonic fogger, a mechanical pressure fogger, or the combination thereof. The type of fogger 6 is chosen under the mist requirements of the liquid, and the present invention is not limited.

Regarding to the structure of present embodiment shown in FIG. 1, the plasma aerosol device of this embodiment allows fogger 6 to create mist based on the fluid of liquid channel 7. At the same time, the dielectric barrier discharge module configured on the output of air channel 8 activates the aforesaid mist thus to form plasma active water mist 9.

The plasma active water mist 9 of this embodiment mainly includes at least one kind of free radicals. In other words, the free radicals must be able to meet specific uses, such as microorganism population control (sterilization), crop nutrient supply or the combination thereof.

Therefore, the at least one free radicals described in this embodiment includes reactive nitrogen species (RNS), reactive oxygen species (ROS) or combinations thereof. More specifically, the reactive nitrogen species (RNS) includes $NO^{3-}$, $NO^{2-}$ or combinations thereof. The reactive oxygen species (ROS) contains $H_2O_2$, $O_3$ or combinations thereof.

Moreover, the type of fluid in the liquid channel 7 can be selected according to different technical fields in the present embodiment. On the other hand, the setting of parameters of the dielectric barrier discharge module can also be switched according to different technical fields and requirements. The present invention is not limited thereto.

Figure 2:
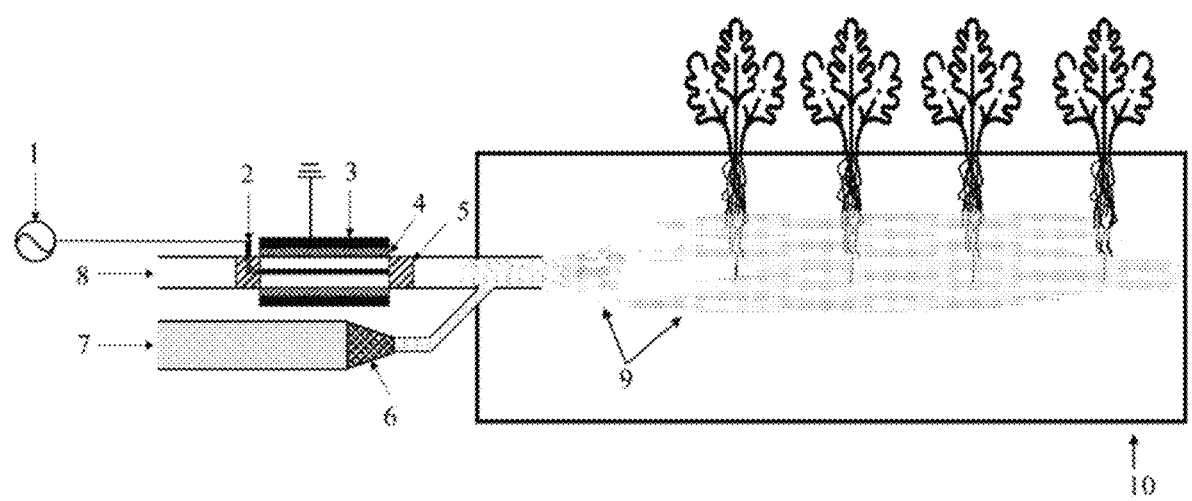
FIG. 2 is a diagram in accordance with one embodiment of using the present invention.

Overall, please refer to FIG. 2, FIG. 2 is a diagram in accordance with one embodiment of using the present invention. In the embodiment of FIG. 2, providing the plasma aerosol device which is shown in FIG. 1 connects to the cultivation box 10. The plasma active water mist 9 produced by the plasma aerosol device riches in reactive nitrogen species (RNS) required by plants such as $NO^{3-}$, and the reactive oxygen species (ROS) which is produced at the same time has antibacterial effects. Therefore, after this embodiment is integrated with the aerosol cultivation technology, reducing the use of chemical fertilizers and pesticides becomes obviously successful. Even in the large-scale farming, this embodiment can be connected in series, parallel, or multi-point spraying, therefore to fulfill the needs of nutrient supply and microorganism population control for numerous kind of plant cultivation.

Similarly, for crops that have been harvested, the embodiment illustrated in FIG. 1 is also able to be installed in a transport vehicle or a crop carrier such as a fresh-keeping box, combining with sensor technology to control the microorganism population. This embodiment greatly reduces the cost of transportation or storage of crops.

That is, due to the active characteristics of reactive nitrogen species (RNS) and reactive oxygen species (ROS), the present embodiment enables plasma active water mist 9 being used well in agricultural planting, transportation, preservation or preservation technology, or used in specific fields such as sterilization or medical treatment.

The present invention is more advantageous than the traditional technologies. All the processes of the present invention only use natural materials such as air and water, without any products that may harmful to the environment, such as traditional chemically synthesized fertilizers, pesticides or disinfectants. The present invention is more environmental-friendly and further reduces the harm to the environment and people.

As is understood by a person skilled in the art, the foregoing preferred embodiments of the present invention are illustrated of the present invention rather than limiting of the present invention. It is intended to cover various modifications and similar arrangements included within the spirit and scope of the appended claims, the scope of which should be accorded the broadest interpretation so as to encompass all such modifications and similar structure. While the preferred embodiment of the invention has been illustrated and described, it will be appreciated that various changes can be made therein without departing from the spirit and scope of the invention.

What is claimed is:

1. A plasma aerosol device, comprising:
   an air channel, comprising an input and an output;
   a dielectric barrier discharge module, configured between the input and the output,
   wherein the dielectric barrier discharge module includes:
     at least two insulators, configured in the air channel;
     a first electrode is inserted between the at least two insulators;
     a power source, connected to the first electrode;
     a dielectric material layer, wrapped around the air channel where the first electrode is inserted;
     a second electrode, grounded and wrapped outside the dielectric material layer; and
     a liquid channel, having a fogger and the liquid channel is connected to the output.

2. The plasma aerosol device as claimed in claim 1, wherein the power source is AC power, a frequency of the power source is between 10-100 kHz; a voltage of the power source is between 5-15 kV; a current of the power source is between 0.001-0.1 A.

3. The plasma aerosol device as claimed in claim 1, wherein the first electrode, the air channel, the dielectric material layer and the second electrode are concentric, tubular shaped elements.

4. The plasma aerosol device as claimed in claim 1, wherein the fogger is a sonic fogger, a mechanical pressure fogger or combinations thereof.

5. The plasma aerosol device as claimed in claim 1, wherein the fogger releases a mist to the output for plasma activation, forming a plasma active water mist.

6. The plasma aerosol device as claimed in claim 1, wherein the fogger releases at least one free radical.

7. The plasma aerosol device as claimed in claim 1, wherein the fogger releases reactive nitrogen species (RNS), reactive oxygen species (ROS) or combinations thereof.

8. The plasma aerosol device as claimed in claim 1, wherein the fogger releases $NO^{3-}$, $NO^{2-}$ or combinations thereof.

9. The plasma aerosol device as claimed in claim 1, wherein the fogger releases $H_2O_2$, $O_3$ or combinations thereof.

* * * * *